United States Patent [19]
Brotzman

[11] Patent Number: 5,563,926
[45] Date of Patent: Oct. 8, 1996

[54] X-RAY CARTRIDGE SUPPORT

[76] Inventor: S. Brent Brotzman, 6270 Strasbourg, Corpus Christi, Tex. 78414

[21] Appl. No.: 558,891

[22] Filed: Nov. 16, 1995

[51] Int. Cl.⁶ .................................................. G03B 42/02
[52] U.S. Cl. .......................... 378/177; 378/167; 378/180
[58] Field of Search ..................................... 378/167, 169, 378/170, 177, 178, 179, 180, 208, 204

[56] References Cited

U.S. PATENT DOCUMENTS

| | | | |
|---|---|---|---|
| 4,414,683 | 11/1983 | Robinson | 378/177 |
| 4,700,373 | 10/1987 | Miller | 378/177 |
| 5,133,000 | 7/1992 | Moller | 378/177 |

FOREIGN PATENT DOCUMENTS

| | | | |
|---|---|---|---|
| 2580488 | 10/1986 | France | 378/177 |

*Primary Examiner*—David P. Porta
*Attorney, Agent, or Firm*—G. Turner Moller

[57] ABSTRACT

A support for an x-ray cartridge includes a base to be placed under the patient having a series of projections or tie downs to which a length of gauze or surgical sponge may be attached. On one end of the base is a U-shaped member for receiving one edge of the x-ray cartridge. An upright U-shaped member is aligned with the first U-shaped member for supporting the cartridge in the aligned groove provided by the U-shaped members. The upright U-shaped member includes one or more projections or tie downs to which the gauze or surgical sponge may be attached. In use, a patient's foot is tied to the base and the upright member to stabilize the foot during exposure by a portable x-ray machine.

19 Claims, 1 Drawing Sheet

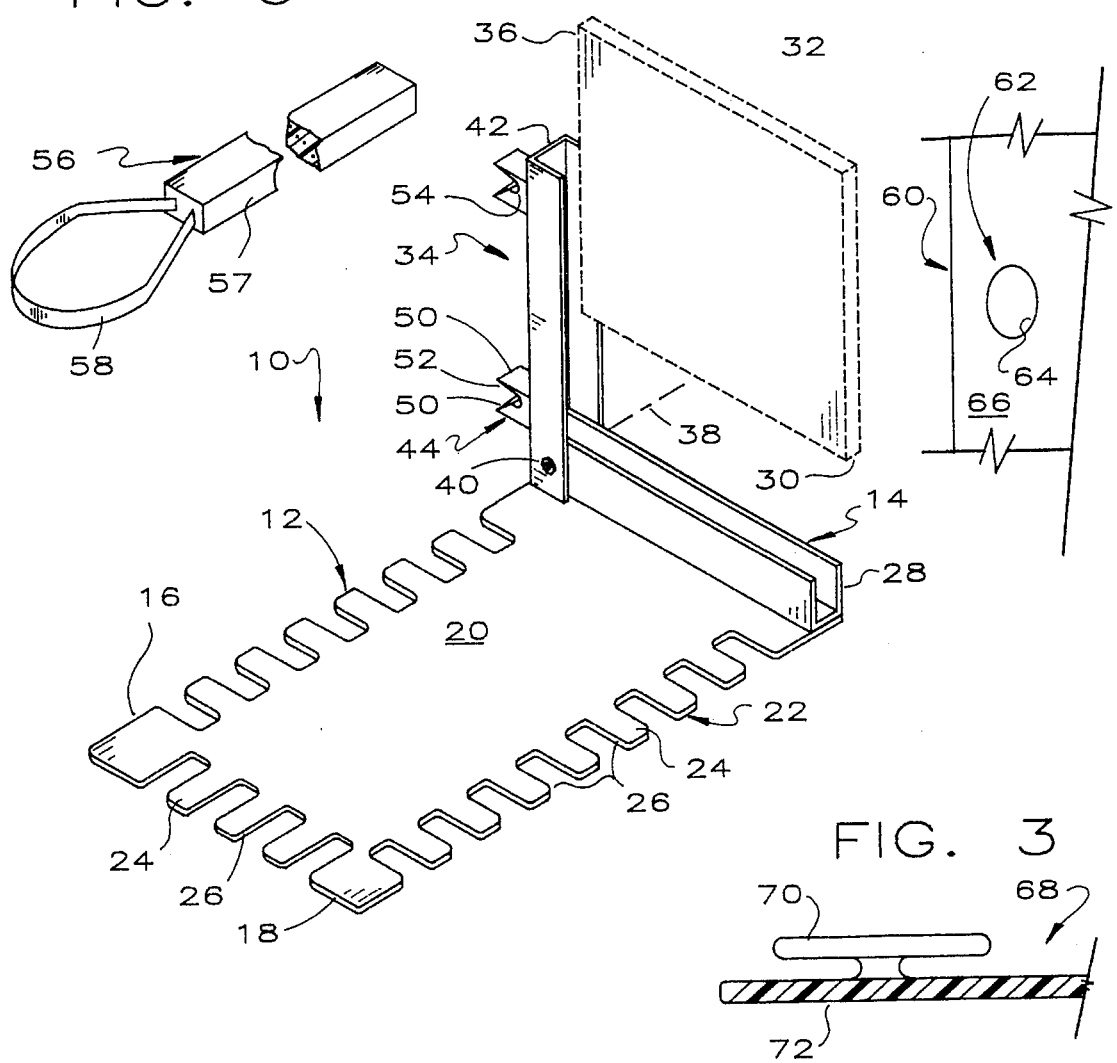

X-RAY CARTRIDGE SUPPORT

This invention is an x-ray cartridge support and, more particularly, a support for holding an x-ray cartridge for use during a surgical operation.

BACKGROUND OF THE INVENTION

Orthopedic surgeons often take x-rays in the middle of a surgical operation for a variety of reasons, such as to determine if a metal plate is properly attached across a bone fracture, to determine if screws placed into a bone are properly positioned and of the correct length, and the like. Most surgeons do not take x-rays during the middle of an operation because most surgical procedures deal with soft tissues which do not show up on x-rays.

To obtain these x-rays, a portable x-ray machine is wheeled into a sterile operating room adjacent the unconscious patient. A conventional x-ray cartridge is wrapped in sterile plastic and placed adjacent the part of the body desired to be x-rayed and is exposed by radiation from the portable x-ray machine. For most surgical operations, this works quite well. For operations on some parts of the body, most notably the foot, there is no convenient way to support the x-ray cartridge while it is being exposed. Despite everyone knowing it is undesirable to expose people to radiation, the common practice is for a doctor, nurse or technician to hold the x-ray cartridge adjacent the patient's foot while it is exposed.

The prior art contains many disclosures of x-ray cartridge supports including U.S. Pat. Nos. 2,568,191; 3,293,430; 3,521,876; 3,892,399; 4,045,678; 4,414,683 and 5,327,912.

SUMMARY OF THE INVENTION

Although this invention has application for x-raying a number of body parts, it is best illustrated and described in x-raying a human foot and will be so described, it being understood that such description is merely exemplary and not restrictive.

This invention includes means to support an x-ray cartridge and means to tie a patient's foot in fixed position adjacent the x-ray cartridge so the cartridge and the foot are stationary during exposure, without requiring operating room personnel to hold either the foot or the cartridge.

The cartridge support includes a base which is normally placed under the patient's leg, thereby stabilizing the device. The base includes a plurality of tie-downs to which a strap, surgical sponge or other suitable tensile element is tied in the course of stabilizing the patient's foot. The tie-downs may be of any suitable type but preferably comprise one or more projections extending away from the base, either parallel to the plane of the base or upright relative to the base.

The cartridge support also includes an L-shaped member of U-shaped cross-section providing a groove to receive a corner of the cartridge. Preferably, the L-shaped member is movable or detachable relative to the base so the device can be collapsed into a generally flat piece for shipping.

It is an object of this invention to provide an improved x-ray cartridge support provided with means to tie a patient's body part to the support.

Another object of this invention is to provide a disposable or reusable x-ray support for stabilizing an x-ray cartridge against a patient's foot.

These and other objects and advantages of this description will become more apparent as this description proceeds, reference being made to the accompanying drawings and appended claims.

BRIEF DESCRIPTION OF THE DRAWINGS

FIG. 1 is an isometric view of one embodiment of this invention;

FIG. 2 is a broken plan view of another embodiment of this invention showing another form of tie-down;

FIG. 3 is a broken cross-sectional view of another embodiment of this invention showing another form of tie-down;

FIG. 4 is a broken cross-sectional view of another embodiment of this invention showing another technique for making the cartridge support of this invention easily shippable;

FIG. 5 is a broken view of another embodiment of this invention showing another technique for making the cartridge support of this invention easily shippable; and FIG. 6 is a broken isometric view of a conventional surgical sponge used as a strap to tie the patient's foot to the support of this invention.

DETAILED DESCRIPTION

Referring to FIG. 1, an x-ray cartridge support 10 of this invention comprises, as major components, a base 12 and an L-shaped cartridge holder 14. The base 12 is such that the patient's leg conveniently lies on top of it to stabilize the support 10. The base 12 is preferably substantially planar or flat.

The foot of an unconscious person, flat on their back, will naturally splay out, i.e. the right foot rotates clockwise toward an inclined or horizontal position while the left foot rotates counterclockwise toward an inclined or horizontal position. The base 12 includes means to tie either foot in a stable position so x-ray film can be exposed with the foot in a desired stationary position.

To this end, the base 12 is generally rectangular having parallel side edges 16 and at least one perpendicular edge 18. The base 12 includes a flat central portion 20 and a plurality of tie-downs 22 to which a strap of any suitable type may be tied to stabilize the patient's foot relative to the support 10. The tie-downs 22 preferably comprise projections 24 provided between a plurality of slots 26 generally perpendicular to the side edges 16 and/or the end edge 18.

The L-shaped cartridge holder 14 includes a first section or channel 28 of U-shaped cross-section which is upwardly opening to receive a bottom edge 30 of a conventional rectilinear, i.e. square or rectangular, x-ray cartridge 32. A second section or channel 34 of the cartridge holder 14 is also of U-shaped cross-section and opens laterally in a plane with the first section 28 to receive a side edge 36 of the x-ray cartridge 32. It will accordingly be seen that the cartridge 32 is held in a stable upright position by the support 10.

Preferably, the cartridge holder 14 is collapsible or detachable to allow convenient shipping. To this end, the second section 34 is preferably pivotally connected to the first section 28 for rotation about a horizontal axis 38, as by the provision of a pair of aligned rivets 40. Thus, the second section 34 is movable from a first nested position relative to the first section 28 and a second upright position where the end of the second section 34 abuts the base 12 thereby limiting pivotal movement of the second section 34. In the upright position of the second section 34, the sections 28, 34 provide aligned slots receiving the x-ray cartridge 32. It will be seen that the second section 34 is movable between an upright support position and a stowed position in a plane parallel to the flat base 12.

Provided on the second section 34, preferably on the back edge 42 comprising the bight of the U-shaped channel, are one or more tie-downs 44 of a size and shape to cooperate with an elongate tensile element 46 such as a strap, length of gauze, surgical sponge or the like. Preferably, the tie-downs 44 are projections extending away from the second section 34 and conveniently comprise a pair of fingers 50 which converge on the facing surfaces 52 and open into a recess 54 larger than the minimum distance between the facing surfaces 52. A tie-down 44 of this type effectively grips a surgical sponge or other elastomeric member when it is pushed into the recess 54.

In use, the support 10 is placed so the base 12 is secure under the patient's leg. The second U-shaped section 34 is raised to its upright position and the x-ray cartridge 32 placed in the aligned grooves of the channels 28, 34. The patient's foot is raised to an upright position and tied to the support 10 in any convenient manner. A surgical sponge 56 is the preferred elongate tensile element for a variety of reasons and conventionally comprises a length of elastomeric material 57 and a radiopaque loop 58 as shown in FIG. 6.

To take an anterior-posterior view of the patient's foot, the patient's foot is tied to the support 10 in a stable upright position. Using the right foot as illustrative, the right foot is placed against the cartridge 32 and the loop 58 of the surgical sponge 56 is tied to the big toe or around the upper part of the foot and connected to one of the tie-downs 44, as by pushing the elastomeric part 57 of the sponge 56 into the recess 54. The end of the sponge 56 is passed diagonally along the back of the cartridge 32 and tied off on one of the projections 24 on the base 12.

To take an x-ray of the side of the right foot, i.e. a lateral radiographic projection, the base 12 is positioned under the patient's foot and leg with the cartridge holder 14 being positioned parallel to the leg. The x-ray cartridge 32 is placed in the slot provided. The loop 58 of the surgical sponge 56 is passed over the patient's big toe or around the upper part of the foot and then tied off on the tie-downs 44. To take a lateral radiographic projection of the left foot, the left foot is stabilized in a similar manner.

The left foot is also easily tied off and stabilized to take an anterior-posterior view. The left foot is placed against the cartridge 32 and the surgical sponge 56 is tied to the big toe or around the upper part of the foot. The surgical sponge 56 is passed around the back of the cartridge 32 and then connected to one of the tie-downs 44, as by pushing the elastomeric part of the sponge 56 into the recess 54 and then wrapping the sponge 56 about the tie-downs 44.

Referring to FIG. 2, another embodiment of an x-ray cartridge support 60 is illustrated having tie-downs 62 in the form of openings 64 in the base 66. It will be seen that an elongate tensile element can be passed through the openings 64 to stabilize the patient's foot.

Referring to FIG. 3, another embodiment of an x-ray cartridge support 68 is illustrated as having cleat type tie-downs 70 projecting upwardly out of the plane of the base 72. It will be seen that an elongate tensile element can be attached to the tie-downs 70.

Referring to FIG. 4, another embodiment of an x-ray cartridge support 74 is illustrated having an L-shaped cartridge holder 76 which is collapsible into a convenient shipping configuration. This is accomplished by fixing the horizontal U-shaped channel 78 to the base 80 and detaching an upright U-shaped channel 82 from the support 74 in any convenient manner, as by snapping one or more connectors 84 of the section 82 into the base 80. It will be seen that the end of the horizontal channel 78 is spaced from the edge of the upright channel 82 but the cartridge support 76 is still sufficient to hold an x-ray cartridge in a stable upright position. The cartridge support 74 is shipped with the upright channel support 82 lying on the base 80 in a plane parallel to the base 80. When it is desired to use the cartridge support 74, the packing materials are removed and the channel support 82 attached to the base 80.

Referring to FIG. 5, another embodiment of an x-ray cartridge support 86 is illustrated having an L-shaped cartridge holder 88 which comprises an upright U-shaped channel 90 fixed to a horizontal U-shaped channel 92. To provide for convenient shipping, the cartridge holder 88 is detachably connected to the base 94, as by snapping one or more connectors 96 on the support 86 into cooperating openings 98 on the base 100. The cartridge support 86 is shipped with the cartridge holder 88 lying on the base 100 in a plane parallel to the base 100. When it is desired to use the cartridge support 86, the packing materials are removed and the cartridge holder 88 attached to the base 100.

Although this invention has been disclosed and described in its preferred forms with a certain degree of particularity, it is understood that the present disclosure of the preferred forms is only by way of example and that numerous changes in the details of operation and in the combination and arrangement of parts may be resorted to without departing from the spirit and scope of the invention as hereinafter claimed.

I claim:

1. A support for receiving a rectilinear x-ray cartridge, comprising a base to be placed under a patient and having at least one tie-down for receiving an elongate tensile element; and an L-shaped cartridge holder comprising a first section of U-shaped cross-section opening away from the base and a second section of U-shaped cross-section transverse to the first section, the first and second sections providing aligned slots for receiving and supporting the rectilinear x-ray cartridge therein in an upright position, the second section providing at least one tie-down for tieing the elongate tensile element to the second section.

2. The support of claim 1 wherein the base includes a generally planar section.

3. The support of claim 2 wherein the tie down on the base comprises a projection generally coplanar with the generally planar section.

4. The support of claim 3 wherein the base includes a plurality of slots opening through an edge of the base and providing the projection between the slots.

5. The support of claim 4 wherein the base provides a pair of parallel first sides generally perpendicular to the first section, the slots opening through the pair of parallel sides and being generally perpendicular to the first sides.

6. The support of claim 5 wherein the base provides a third side perpendicular to the first sides, there being a plurality of slots opening through the third side and providing at least one projection between the slots.

7. The support of claim 1 wherein the base includes a generally flat section and the tie-down comprises a projection on the base extending upwardly away from the flat section.

8. The support of claim 1 wherein the tie-down on the base comprises an opening in the base.

9. The support of claim 1 wherein the second section includes a bight and a pair of legs extending away from the bight and providing the U-shaped cross-section and the tie-down on the second section comprises a projection extending away from the bight.

10. The support of claim 1 further comprising means for placing the second section in a plane parallel to the first section.

11. The support of claim 10 wherein the second section is pivotally mounted to the first section.

12. The support of claim 10 wherein the second section is detachable from the cartridge support.

13. The support of claim 12 wherein the second section is detachable from the base.

14. The support of claim 10 wherein the first section is detachably affixed to the base.

15. A support for receiving a rectilinear x-ray cartridge, comprising a base to be placed under a patient; and an L-shaped cartridge holder comprising a first section of upwardly opening U-shaped cross-section affixed to the base and a second section of U-shaped cross-section generally perpendicular to the first section, the first and second sections providing aligned slots for receiving and supporting the rectilinear x-ray cartridge therein in an upright position, the second section providing at least one tie-down projecting away from a bight of the second section for tieing the elongate tensile element to the second section.

16. A support for receiving a rectilinear x-ray cartridge, comprising a base to be placed under a patient;

an L-shaped cartridge holder comprising a first section of U-shaped cross-section opening away from the base and a second section of U-shaped cross-section transverse to the first section, the first and second sections providing aligned slots for receiving and supporting the rectilinear x-ray cartridge therein in an upright position, the second section providing at least one tie-down for tieing the elongate tensile element to the second section; and means for placing the second section in a plane parallel to the first section.

17. The support of claim 16 wherein the second section is pivotally mounted to the first section.

18. The support of claim 16 wherein the second section is detachable from the cartridge support.

19. A support for receiving a rectilinear x-ray cartridge, comprising a base to be placed under a patient and having at least one tie-down for receiving an elongate tensile element; and an L-shaped cartridge holder comprising a first section of U-shaped cross-section opening away from the base and a second section of U-shaped cross-section transverse to the first section, the first and second sections providing aligned slots for receiving and supporting the rectilinear x-ray cartridge therein in an upright position.

\* \* \* \* \*